United States Patent [19]

Wall

[11] 4,032,589

[45] June 28, 1977

[54] DEHYDROGENATION CATALYST AND PROCESS

[75] Inventor: Robert G. Wall, Pinole, Calif.

[73] Assignee: Chevron Research Company, San Francisco, Calif.

[22] Filed: Mar. 17, 1975

[21] Appl. No.: 559,288

[52] U.S. Cl. .......................... 260/683.3; 260/673; 208/138; 252/465
[51] Int. Cl.² ............................................ C07C 5/18
[58] Field of Search .................... 260/683.3, 673; 208/138; 252/465

[56] References Cited

UNITED STATES PATENTS 3,531,543   9/1970   Clippinger et al. ............. 260/683.3

*Primary Examiner*—Vernoica O'Keefe
*Attorney, Agent, or Firm*—Dix A. Newell; John Stoner, Jr.; W. Keith Turner

[57] ABSTRACT

A process for dehydrogenating an alkane which comprises contacting the alkane under dehydrogenation conditions including a temperature between 400 and 800° C with a catalyst comprising platinum, chromium, lithium and alumina.

Preferably the catalyst comprises 0.1 to 1 weight percent platinum, 0.1 to 1 weight percent chromium, 0.1 to 1 weight percent lithium, and 97 to 99.7 weight percent alumina.

6 Claims, No Drawings

DEHYDROGENATION CATALYST AND PROCESS

BACKGROUND OF THE INVENTION

The present invention relates to a dehydrogenation catalyst and process using the catalyst, especially a platinum-chromium-lithium-alumina catalyst.

Catalytic dehydrogenation processes are well known and are discussed in general by Kearby in Chapter 10, pages 453–491, of Catalysis, Vol. III, edited by P. H. Emmett, Reinhold Publishing Corporation (1955). Exemplary dehydrogenation reactions are:

1. Propane → propene + $H_2$
2. Butene → butadiene + $H_2$
3. Ethylbenzene → styrene + $H_2$
4. Butane → butadiene + $2H_2$ Typical dehydrogenation temperatures are between 400° and 800° C, and typical pressures are 0.1 to 100 atmospheres.

The Catalysis Chapter 10 reference cited above summarizes various dehydrogenation catalysts, for instance at pages 463 and 475, including the well-known chromia-alumina catalyst. According to the Beeck reference (Nature, 136, page 1028 (1935)) discussed in the Catalysis Chapter 10 reference referred to above, appreciably less severe dehydrogenation conditions were required when components such as oxides of chromium, vanadium, iron, zinc or nickel were added to activated alumina used for dehydrogenating isobutane in the presence of small amounts of water. Also, of the materials tested by Beeck, the chromia-on-alumina was reported to give the best results.

U.S. Pat. No. 2,956,030 discloses that typical commercial chromia-alumina dehydrogenation catalysts are prepared using activated alumina having a surface area of about 80 square meters per gram. The alumina is impregnated with chromic acid, dried, and calcined to obtain a finished catalyst having about 20 weight percent chromia and a surface area of about 50–60 square meters per gram. According to U.S. Pat. No. 2,956,030 an improved catalyst is provided using a particular type of alumina (gamma alumina) and an alkali metal content controlled to lie in the well-defined range of about 0.15 to 0.5% alkali metal oxide by weight of the catalyst. Also somewhat higher surface area alumina is used as the catalyst support, preferably 150 m²/g or more.

U.S. Pat. No. 2,870,084 discloses the use of a chromia-platinum-alumina catalyst for aromatizing a naphtha feed. The catalyst used is a coprecipitated alumina-chromia catalyst having 70–82 mol percent alumina, 30–18 mol percent chromia, and 0.001 to 1.0 mol percent platinum oxide or palladium oxide.

U.S. Pat. No. 3,554,901 discloses the use of a chromium-platinum-palladium-alumina catalyst for aromatizing hydrocarbons. The catalyst is prepared by impregnating a carrier such as silica or alumina or silica-alumina with .1 to 1.0 weight percent platinum, .1 to 1.0 percent palladium, and 5 to 25 percent chromium oxide.

U.S. Pat. No. 3,780,129 discloses the use of a chromic oxide-nickel-lithium-alumina catalyst for dehydrogenation of hydrocarbons, as, for example, dehydrogenation of n-butane to obtain butenes and butadiene, and dehydrogenation of isopentane to obtain isoamylenes and isoprene. According to the example in U.S. Pat. No. 3,780,129, the catalyst was prepared by mixing commercially available alumina-chromia catalyst with nickel nitrate, lithium nitrate, and additional inert alpha-alumina followed by drying and calcining. The claimed catalyst consists essentially of 1–40% by weight chromium oxide, 0.01–0.1% nickel oxide, 0.1–10% lithium oxide, and the remainder alumina.

The use of alkali metals in dehydrogenation catalysts has been disclosed, for example, in U.S. Pat. No. 3,126,426: platinum group metal on alumina with a large amount, preferably over 5 weight percent, of alkali metals such as potassium; U.S. Pat. No. 3,119,883: zinc oxide plus iron, tin, or bismuth plus less than 1 weight percent alkali metal; U.S. Pat. Nos. 3,363,023: chromia plus magnesia plus alkali metal on an alumina support; and 3,439,061, Group VIII noble metal sulfide on a silica support.

The use of four-component dehydrogenation catalysts has been disclosed in several patents to Haensel and Block, for example U.S. Pat. Nos. 3,293,319; 3,291,755; 3,291,855; 3,391,218; 3,448,165; 3,448,166; and 3,682,838. According to U.S. Pat. No. 3,293,319 the dehydrogenation catalyst for dehydrogenating saturated hydrocarbons comprises about 0.01–1.5 weight percent lithium, from about 0.05 to 5 weight percent Group VIII metal component, and a further metal component selected from arsenic, antimony, and bismuth. Typically an alumina support is used for the catalyst.

U.S. Pat. No. 3,531,543 discloses a dehydrogenation catalyst which comprises a Group VIII noble metal, tin, a support such as alumina, and a neutralizing component such as lithium.

Japanese pat. appln. No. 084972 discloses a dehydrogenation catalyst containing platinum and chromium and platinum-chromium polyphthalocyanine on a porous support, which support does not contain lithium.

SUMMARY OF THE INVENTION

According to the present invention a process is provided for dehydrogenating an alkane, which process comprises contacting the alkane under dehydrogenation conditions including a temperature between 850° and 1250° F with a catalyst comprising platinum, chromium, lithium and alumina.

Among other factors, the present invention is based on my unexpected finding that chromium addition to a platinum-lithium-alumina catalyst markedly improves the selectivity of the catalyst for dehydrognation of alkanes to alkenes.

Preferably the catalyst comprises 0.05 to 5 weight percent platinum, 0.05 to 5 weight percent chromium, 0.05 to 5 weight percent lithium, and 85 to 99.85 weight percent alumina. More preferably, the catalyst comprises 0.1 to 1 weight percent platinum, 0.1 to 1 weight percent chromium, 0.1 to 1 weight percent lithium, and 97 to 99.7 weight percent alumina. According to a preferred embodiment, the catalyst also contains 0.1 to 1.0 weight percent tin.

The feed to the process of the present invention is a dehydrogenatable hydrocarbon, especially a hydrocarbon having a saturated carbon-carbon bond as in an alkane. Preferably the feed is a $C_2$–$C_{20}$ alkane, more preferably propane, n-butane, i-butane, a dehydrogenatable pentane, or a hexane.

Preferred operating conditions include:

|                              | Preferred | More Preferred |
|------------------------------|-----------|----------------|
| Temperature, °F              | 850–1250  | 900–1150       |
| Pressure, atm.               | 0.1–3     | 1–2            |
| Liquid Hourly Space Velocity | 1–40      | 1–20           |
| $H_2$/Hydrocarbon Molar Ratio| 0.5–20    | 1–10           |

The components of the catalyst of the present invention may be present in compound form. For example, chromium typically is present in the finished catalyst as the oxide compound, and lithium is also typically present as an oxide.

EXAMPLES

Example 1: Preparation of Pt on lithiated alumina

A solution of 0.50 g tetrammine platinuos nitrate and 2.52 g lithium nitrate in 20 ml of water was poured onto 50 g of Houdry HA100S 16-32 mesh alumina. Most of the water was removed by evaporation under vacuum. Calcination in air was carried out for 1 hour at 600° F, 1 hour at 800° F and 1 hour at 1000° F. Calculated composition is 0.5% Pt and 0.5% Li on alumina.

Example 2: Preparation of Pt-Cr-Li on alumina

An aqueous solution containing 0.1 g tetrammine platinous nitrate, 0.5 g lithium nitrate and 0.38 g $Cr(NO_3)_3 9H_2O$ was poured onto 10 g Houdry HA100S alumina. The catalyst was calcined 1 hour at 600° F, 1 hour at 800° F and 2 hours at 1000° F. Calculated composition is 0.5% Pt, 0.5% Cr and 0.5% Li on alumina.

Example 3: Preparation of Pt-Cr-Li-Sn on alumina

A solution of 0.1 g tetrammine platinous nitrate, 0.5 g lithium nitrate and 0.38 g $Cr(NO_3)_3 9H_2O$ in 5 ml of water was added to 10 g Houdry HA100S 16-32 mesh alumina. Most of the water was removed under vacuum before drying 2 hours at 130° C. A solution of 0.1 g tetra-n-butyl tin in 5 ml pentane was added and the material dried as above. The catalyst was calcined in air for 1 hour at 600° F, 1 hour at 800° F and 2 hours at 1000° F. Calculated compositions is 0.5% Pt, 0.5% Cr, 0.5% Li and 0.3% Sn on alumina.

Example 4: Preparation of Pt-Li-Sn on Alumina

A solution of 0.1 g tetrammine platinous nitrate and 0.5 g lithium nitrate in 5 ml of water was added to 10 g Houdry HA100S 16-32 mesh alumina. Most of the water was removed under vacuum before drying 2 hours at 130° C. A solution of 0.1 g tetra-n-butyl tin in 5 ml pentane was added and the material dried as above. The catalyst was calcined in air for 1 hour at 600° F, 1 hour at 800° F and 2 hours at 1000° F. Calculated compositions is 0.5% Pt, 0.5% Cr, 0.5% Li and 0.3% Sn on alumina.

Example 5: Dehydrogenation runs

In each case 2 ml of catalyst was mixed with 2 ml of alundum and supported in a ⅜ inch O.D. thick-walled stainless-steel reactor tube. The catalysts were pretreated for 16–64 hours with $H_2$ at 900 F before each run. Runs were made at 900° F with a feed rate of 2 cc/hr of liquid isobutane and 50 cc/min of hydrogen at 1 atm pressure (LHSV=1, $H_2/iC_4$=6). Results are shown below in Table I; the product was analyzed by gas-phase chromatography:

Table I

| Catalyst                | (1)       | (2)       | (3)         | (4)       |
|-------------------------|-----------|-----------|-------------|-----------|
| Metals                  | Pt-Li     | Pt-Li-Cr  | Pt-Li-Cr-Sn | Pt-Li-Sn  |
| Products (area%):       |           |           |             |           |
| Lights ($C_3-$)         | 4–5%      | 2–2.3%    | Trace       | Trace     |
| Isobutane               | 74–79%    | 83–85%    | 91.6–91.8%  | 91.5–91.7%|
| Isobutylene             | 6–6.4%    | 6.6–6.8%  | 8.2–8.4%    | 7.9–8.3%  |
| n-butane + n-butene     | 11–14%    | 6.8–7.6%  | —           | —         |

Example 6

In another comparison at 1100° F, LHSV=3.5 and $H_2$/isobutane ratio of 4 the following results were obtained:

Table II

| Catalyst              | (3)         | (4)       |
|-----------------------|-------------|-----------|
| Metals                | Pt-Li-Cr-Sn | Pt-Li-Sn  |
| Conversion of isobutane | 47%       | 45%*      |
| Yield of isobutylene  | 97.5%       | 96%*      |

*These results taken from U.S. Patent 3,531,543.

The above results illustrate improvement in terms of increased isobutylene yield and lights production (losses) decrease using the PtLiCr catalyst compared to the PtLi catalyst. Even though Li was already present to reduce the acidity of the alumina, the Cr in the PtLiCr combination surprisingly still further reduced lights production and improved dehydrogenation to isobutylene.

The PtLiCr catalyst was also discovered to result in substantially less of the undesired isomerization of isobutane to n-butane and hence n-butene compared to dehydrogenation with the PtLi catalyst.

With the added Sn component the PtLiCr catalyst performed very well, as shown in Table II. It was unexpected that the PtLiCrSn combination would show improved yields over the PtLiSn catalyst.

I claim:

1. A process for dehydrogenating a $C_2$ to $C_{20}$ alkane or mixtures thereof which comprises contacting the alkane with a catalyst comprising 0.1 to 1 weight percent platinum, 0.1 to 1 weight percent chromium, and 0.1 to 1 weight percent lithium and an alumina support, wherein the dehydrogenation is carried out under conditions including a temperature between 850° and 1250° F, a liquid hourly space velocity between 1 and 40, and a hydrogen to alkane molar ratio between 0.5 and 20.

2. A process in accordance with claim 1 wherein the temperature is 900° to 1150° F and the feed alkane is propane, n-butane, i-butane, a dehydrogenatable pentane, or a hexane.

3. A process in accordance with claim 1 wherein the chromium and lithium are present in the catalyst in the oxide form.

4. A process of dehydrogenating a $C_2$ to $C_{20}$ alkane or mixtures thereof which comprises contacting the alkane with a catalyst consisting essentially of 0.1 to 1 weight percent platinum, 0.1 to 1 weight percent chromium, and 0.1 to 1 weight percent lithium and an alumina support, wherein the dehydrogenation is carried out under conditions including a temperature between 850° and 1250° F, a liquid hourly space velocity between 1 and 40, and a hydrogen to alkane molar ratio between 0.5 and 20.

5. A process in accordance with claim 4 wherein the temperature is 900° to 1150° F and the feed alkane is propane, n-butane, i-butane, a dehydrogenatable pentane, or a hexane.

6. A process in accordance with claim 4 wherein the chromium and lithium are present in the catalyst in the oxide form.

* * * * *